US007320878B2

(12) United States Patent
Gulnik et al.

(10) Patent No.: US 7,320,878 B2
(45) Date of Patent: Jan. 22, 2008

(54) PROTEASE ASSAY FOR THERAPEUTIC DRUG MONITORING

(75) Inventors: Sergei Gulnik, Frederick, MD (US); Betty Yu, Frederick, MD (US); John W Erickson, Potomac, MD (US); Martin Markowitz, New York, NY (US)

(73) Assignees: Tibotec Pharmaceuticals, Ltd. (IR); Aaron Diamond Aids Research Center, New York, NY (US); The Rockefeller University, New York, NY (US)

( * ) Notice: Subject to any disclaimer, the term of this patent is extended or adjusted under 35 U.S.C. 154(b) by 0 days.

(21) Appl. No.: 10/494,903

(22) PCT Filed: Nov. 8, 2002

(86) PCT No.: PCT/EP02/12631

§ 371 (c)(1),
(2), (4) Date: Nov. 4, 2004

(87) PCT Pub. No.: WO03/040390

PCT Pub. Date: May 15, 2003

(65) Prior Publication Data

US 2005/0221286 A1 Oct. 6, 2005

Related U.S. Application Data

(60) Provisional application No. 60/331,117, filed on Nov. 8, 2001.

(51) Int. Cl.
*C12Q 1/37* (2006.01)
*G01N 33/53* (2006.01)

(52) U.S. Cl. .......................... 435/23; 435/24; 435/7.72

(58) Field of Classification Search ..................... None
See application file for complete search history.

(56) References Cited

U.S. PATENT DOCUMENTS

| 4,546,076 A | 10/1985 | Degelaen et al. .............. 435/24 |
| 4,918,001 A | 4/1990 | Kolde ........................... 435/24 |
| 5,576,177 A | 11/1996 | Fridland et al. ................. 435/5 |
| 5,843,946 A | 12/1998 | Vazquez et al. ............. 514/252 |
| 6,017,723 A * | 1/2000 | Rao et al. ....................... 435/18 |
| 6,243,980 B1 * | 6/2001 | Bronstein et al. ........... 435/7.72 |

FOREIGN PATENT DOCUMENTS

| EP | 0 428 000 A1 | 5/1991 |
| EP | 0 518 557 B1 | 12/1992 |
| WO | WO 97/27319 | 7/1997 |
| WO | WO 97/27480 | 7/1997 |
| WO | WO 99/50579 | 10/1999 |
| WO | WO 99/54734 | 10/1999 |
| WO | WO 99/67417 | 12/1999 |
| WO | WO 01/57245 A2 | 8/2001 |
| WO | WO 02/23186 A2 * | 9/2001 |
| WO | WO 01/79540 A2 | 10/2001 |
| WO | WO 02/23186 A2 | 3/2002 |
| WO | WO 02/38792 | 5/2002 |

OTHER PUBLICATIONS

Guidance for Industry; U.S. Food and Drug Administration, Center for Drug Evaluation and Research, Center for Biologics Evaluation and Research, Nov. 1999.☐☐Http://www.fda.gov/cder/guidance/2635fnl.pdf.*
Zhang et al. Drur Resistance During Indinavir Therapy is Caused by Mutations in the Protease Gene and in its Gag Substrate Cleavage Sites: Journal of Virology, vol. 71, No. 9 (1997) pp. 6662-6670.*
Vance et al. Conformational Selectivity of HIV-1 Protease Cleavage of X-Pro Peptide Bonds and its Implications; The Journal of Biological Chemistry, vol. 272, No. 25 (1997) pp. 15603-15606.*
Aarnoutse, Re, et al., "High-Performance Liquid Chromatography of HIV-Protease Inhibitors in Human Biological Matrices" *Journal of Chromatography*, 2001, 764, 363-384.
Dailly, E. et al., "High-Performance Liquid Chromatographic Assay to Determine the Plasma Levels of HIV-Protease Inhibitors (Amprenavir, Indinavir, Nelfinavir, Ritonavir and Saquinavir) and the Non-Nucleoside Reverse Transcriptase Inhibitor (Nevirapine) after Liquid-Liquid Extraction", *Journal of Chromatography B* 2001, 758(2), 129-135.
Gulnik, S. et al., "Enzymatic Bioassay for Therapeutic Drug Monitoring of HIV Protease Inhibitors", *Antiviral Therapy*, 2002, 7, S78.
Kakiuchi, N., et al. "A High Throughput Assay of the Hepatitis C Virus Nonstructural Protein 3 Serine Proteinase", *Journal of Virological Methods*, 1999, 80, 77-84.
Leela, John et al., "Role of Therapeutic Drug Monitoring for Protease Inhibitors", *The Annals of Pharmacotherapy*, 2001, 35(6), 745-754.
Marzolini, C. et al., "Simultaneous Determination of the HIV Protease Inhibitors Indinavir, Amprenavir, Saquinavir, Ritonavir, Nelfinavir and the Non-Nucleoside Reverse Transcriptase Inhibitor Efavirenz by High-Performance Liquid Chromatography after Solid-Phase Extraction", *Journal of Chromatography B.*, 2000, 740(1), 43-58.
Matayoshi, E.D. et al., "Novel Flurogenic Substrates for Assaying Retroviral Proteases by Resonance Energy Transfer", *Science*, 1990, 247, 954-958.
Moyle, GJ. et al., "Principles and Practice of HIV-Protease Inhibitor Pharmacoenhancement", *HIV Medicine*, 2001, 2, 105-113.

(Continued)

*Primary Examiner*—Jon Weber
*Assistant Examiner*—Paul Martin
(74) *Attorney, Agent, or Firm*—Woodcock Washburn LLP

(57) ABSTRACT

The present invention concerns a further development and use of biological assays to determine the amount or concentration of an active ingredient present in a sample. The enzyme assay of the present invention determines the amount or concentration of protease inhibitors, including retroviral protease inhibitors such as HIV inhibitors.

16 Claims, 7 Drawing Sheets

OTHER PUBLICATIONS

Figure 1:
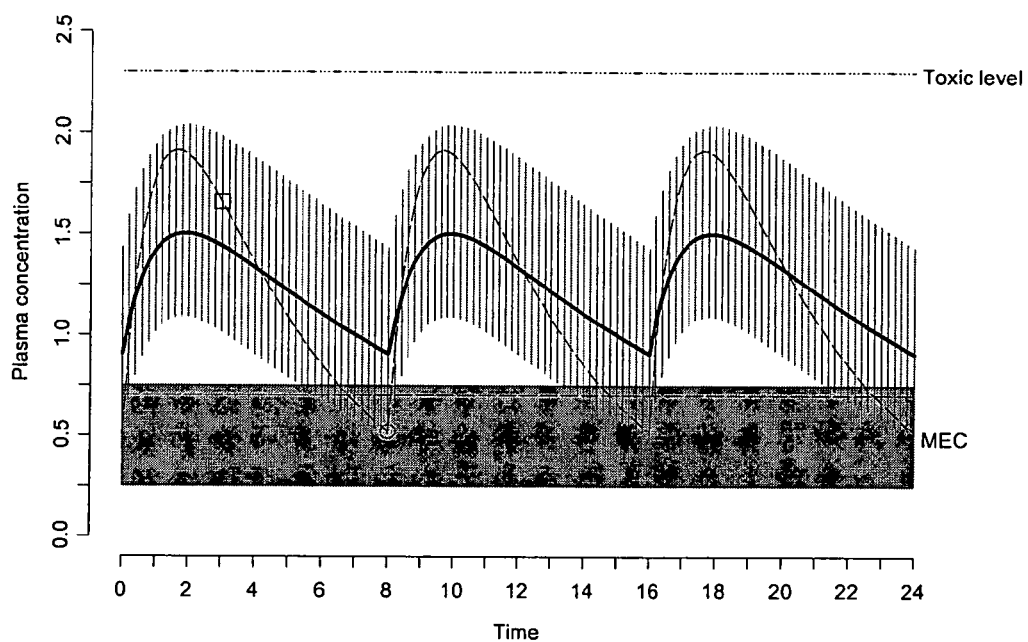

Taliani, M. et al., "A Continuous Assay of Hepatitis C Virus Protease Based on Resonance Energy Transfer Depsipeptide Substrates", *Analytical Biochemistry*, 1996, 240, 60-67.

Zhang, R. et al., "A Continuous Spectrophotometric Assay for the Hepatitis C Virus Serine Protease", *Analytical Biochemistry*, 1999, 270, 268-275.

Toth, M.V. et al., "A Simple, Continuous Flurometric Assay for HIV Protease", *Int. J. Peptide Protein Res.*, 1990, 36(6), 544-550.

Tyagi, S.C. et al., "Continuous Assay of the Hyrdolytic Activity of Human Immunodeficiency Virus-1 Protease", *Analytical Biochemistry*, 1992, 200(1), 143-148.

Villani, P. et al., "Antireovirals: Simultaneous Determination of Five Protease Inhibitors and Three Nonnucleoside Transcriptase Inhibitors in Human Plasma by a Rapid High-performance Liquid Chromatography-Mass Spectrometry Assay", *Therapeutic Drug Monitoring.*, 2001, 23(4),380-388.

Wang, G.T. et al., "Design and Synthesis of New Flurogenic HIV Protease Substrates Based on Resonance Energy Transfer", *Tetrahedron Letters*, 1990, 31(45), 6493-6496.

Warner, A., "Setting Standards of Practice in Therapeutic Drug Monitoring and Clinical Toxicology: A North American View", *Therapeutic Drug Monitoring*, 2001, 23(2),93-97.

\* cited by examiner standards (nM)

| Sample | Concentration | Wells | Values | StDev | CV% | MeanValue | Ratio |
|---|---|---|---|---|---|---|---|
| Sa01 | 0.000 | A1 | 3306.381 | 111.302 | 3.288 | 3385.083 | 1.00 |
| | | A2 | 3463.786 | | | | |
| Sa02 | 10.000 | B1 | 3368.743 | 45.115 | 1.352 | 3336.842 | 0.99 |
| | | B2 | 3304.940 | | | | |
| Sa03 | 25.000 | C1 | 3041.364 | 57.563 | 1.868 | 3082.067 | 0.91 |
| | | C2 | 3122.770 | | | | |
| Sa04 | 40.000 | D1 | 2323.149 | 24.691 | 1.071 | 2305.680 | 0.68 |
| | | D2 | 2288.230 | | | | |
| Sa05 | 50.000 | E1 | 2029.726 | 9.713 | 0.480 | 2022.858 | 0.60 |
| | | E2 | 2015.989 | | | | |
| Sa06 | 60.000 | F1 | 1488.507 | 40.983 | 2.808 | 1459.528 | 0.43 |
| | | F2 | 1430.549 | | | | |
| Sa07 | 75.000 | G1 | 1308.329 | 26.099 | 2.023 | 1289.875 | 0.38 |
| | | G2 | 1271.420 | | | | |
| Sa08 | 100.000 | H1 | 357.519 | 44.751 | 13.733 | 325.875 | 0.10 |
| | | H2 | 294.232 | | | | |

Smallest standard value: 325.875
Largest standard value: 3385.083

Figure 4 mini4

| Sample | Wells | Values | MeanValue | StDev | CV% | Ratio | Result | Dilution | Adj.Result |
|---|---|---|---|---|---|---|---|---|---|
| 0.5 | B9 | 4648.795 | 4702.606 | 76.10 | 1.62 | 0.97 | 6.702 | 120.0 | 804.28 |
|  | B10 | 4756.416 |  |  |  |  |  |  |  |
| 1 | C9 | 4172.748 | 4303.960 | 185.56 | 4.31 | 0.88 | 20.347 | 60.0 | 1220.85 |
|  | C10 | 4435.171 |  |  |  |  |  |  |  |
| 3 | D9 | 3203.885 | 3354.045 | 212.36 | 6.33 | 0.69 | 52.882 | 20.0 | 1057.24 |
|  | D10 | 3504.206 |  |  |  |  |  |  |  |
| 5 | E9 | 2039.743 | 2070.693 | 43.77 | 2.11 | 0.43 | 96.789 | 12.0 | 1161.47 |
|  | E10 | 2101.643 |  |  |  |  |  |  |  |
| 10 | F9 | -38.149 | -37.271 | 1.24 | 3.33 | -0.01 | 168.942 | 6.0 | 1013.65 |
|  | F10 | -36.394 |  |  |  |  |  |  |  |
| 30 | G9 | -49.867 | -50.258 | 0.55 | 1.10 | -0.01 | 169.387 | 2.0 | 338.77 |
|  | G10 | -50.650 |  |  |  |  |  |  |  |
| 60 | H9 | -78.446 | -81.582 | 4.43 | 5.44 | -0.02 | 170.459 | 1.0 | 170.46 |
|  | H10 | -84.717 |  |  |  |  |  |  |  |

R - Outside standard range

Mean Adjusted Result: 310.52

Figure 6

Summary of accuracy (with error) and precision (with CV%) tests

| Real conc (nM) | 50 | 100 | 1000 | 10000 |
|---|---|---|---|---|
| Exp.1 (Error) |  | 120 (20%) | 933.1 (6.7%) | 10404.5 (4%) |
| Exp.2 (Error) | 60.2 (20.4%) | 109.1 (9.1%) | 1131.2 (13.1%) | 11975.2 (19.7%) |
| Exp.3 (Error) | 45.2 (9.6%) | 82.5 (17.5%) | 839.2 (16.1%) | 11232.7 (12.3%) |
| Exp.4 (Error) | 64.9 (25.8%) | 112 (12%) | 1094 (9.4%) | 12493.6 (24.9%) |
| Exp.5 (Error) | 57.8 (15.6%) | 114.7 (14.7%) | 897.2 ((10.3%) |  |
| Mean | 57 | 107.66 | 978.94 | 11527 |
| StDev | 8.42 | 14.627 | 127.21 | 909.54 |
| CV% | 14.8 | 13.6 | 13 | 7.9 |

*Validation test*

Figure 7

SEQUENCE LISTING

```
<160> NUMBER OF SEQ ID NOS: 10

<210> SEQ ID NO 1
<211> LENGTH: 8
<212> TYPE: PRT
<213> ORGANISM: Artificial
<220> FEATURE:
<223> OTHER INFORMATION: Synthetic Construct

<400> SEQUENCE: 1

Ser Gln Asn Thr Pro Ile Val Asn
1               5

<210> SEQ ID NO 2
<211> LENGTH: 9
<212> TYPE: PRT
<213> ORGANISM: Artificial
<220> FEATURE:
<223> OTHER INFORMATION: Synthetic Construct

<400> SEQUENCE: 2

Ser Gln Asn Tyr Pro Ile Val Trp Leu
1               5

<210> SEQ ID NO 3
<211> LENGTH: 9
<212> TYPE: PRT
<213> ORGANISM: Artificial
<220> FEATURE:
<223> OTHER INFORMATION: Synthetic Construct

<400> SEQUENCE: 3

Ser Gln Asn Tyr Pro Ile Val Gln Lys
1               5

<210> SEQ ID NO 4
<211> LENGTH: 3
<212> TYPE: PRT
<213> ORGANISM: Artificial
<220> FEATURE:
<223> OTHER INFORMATION: Synthetic Construct

<400> SEQUENCE: 4

Pro Ile Val
1

<210> SEQ ID NO 5
<211> LENGTH: 4
<212> TYPE: PRT
<213> ORGANISM: Artificial
<220> FEATURE:
```

```
<223> OTHER INFORMATION: Synthetic Construct

<400> SEQUENCE: 5

Tyr Pro Ile Val
1

<210> SEQ ID NO 6
<211> LENGTH: 7
<212> TYPE: PRT
<213> ORGANISM: Artificial
<220> FEATURE:
<223> OTHER INFORMATION: Synthetic Construct

<400> SEQUENCE: 6

Ala Arg Val Tyr Phe Glu Ala
1               5

<210> SEQ ID NO 7
<211> LENGTH: 10
<212> TYPE: PRT
<213> ORGANISM: Artificial
<220> FEATURE:
<223> OTHER INFORMATION: Synthetic Construct

<400> SEQUENCE: 7

Asp Asp Ile Val Pro Cys Ser Met Ser Lys
1               5                   10

<210> SEQ ID NO 8
<211> LENGTH: 11
<212> TYPE: PRT
<213> ORGANISM: Artificial
<220> FEATURE:
<223> OTHER INFORMATION: Synthetic Construct

<400> SEQUENCE: 8

Asp Asp Ile Val Pro Cys Ser Met Lys Arg Arg
1               5                   10

<210> SEQ ID NO 9
<211> LENGTH: 7
<212> TYPE: PRT
<213> ORGANISM: Artificial
<220> FEATURE:
<223> OTHER INFORMATION: Synthetic Construct

<400> SEQUENCE: 9

Asp Thr Glu Asp Val Val Pro
1               5

<210> SEQ ID NO 10
<211> LENGTH: 12
<212> TYPE: PRT
<213> ORGANISM: Artificial
<220> FEATURE:
<223> OTHER INFORMATION: Synthetic Construct

<400> SEQUENCE: 10

Arg Glu Ser Gln Asn Tyr Pro Ile Val Gln Lys Arg
1               5                   10
```

PROTEASE ASSAY FOR THERAPEUTIC DRUG MONITORING

CROSS-REFERENCE TO RELATED APPLICATIONS

This application is the National Stage of International Application No. PCT/EP02/12631, filed Nov. 8, 2002, which claims the benefit of U.S. Provisional Application No. 60/331,117, filed Nov. 8, 2001, the disclosure of which is incorporated herein by reference.

Qualitative and quantitative assays are of great importance in different fields of the life sciences. The present invention concerns the use of biological assays to determine the amount or concentration of an active ingredient present in a sample. In particular, the enzyme assay of the present invention determines the amount or concentration of protease inhibitors, including retroviral protease inhibitors such as human immunodeficiency virus protease inhibitors, in a sample.

Therapeutic drug monitoring plays an important role in follow-up of treatment efficacy. In order to achieve a therapeutic effect, drugs acting as enzyme inhibitors should be administered in dosages that provide sufficient inhibition of the enzyme involved. Diagnostic tools have been developed to monitor the therapeutic effect of drugs in a patient at a certain concentration.

Current day monitoring assays for HIV (human immunodeficiency virus, HIV) inhibitors rely on techniques such as thin layer chromatography (TLC), high pressure liquid chromatography (HPLC), mass spectrometry (MS) and liquid chromatography-mass spectrometry (LC-MS) [Ther. Drug Monit. 2001, 23(4), 380; J. Chromatogr. B Biomed Sci. Appl (2001), 758(2), 129; J. Chromatogr. B Biomed Sci. Appl (2000), 740(1), 43]. Though these methods can monitor simultaneously several inhibitors in a single patient sample, these assays do not provide a measure of inhibition of the target enzyme. Leela et al. report that current methods for determining HIV inhibitors are not routinely available in a clinical laboratory and that a simplified, less tedious assay is needed and still needs to be developed. [Ann. Pharmacother. 2001, 35(6), 745].

The use of enzymes to monitor drug concentrations was described in e.g. U.S. Pat. Nos. 4,918,001, 4,546,076, 5,576,177 and WO 99/54734. The latter patent publication discloses the use of coated pins that are inserted into a solution. For instance, if the pins are coated with a substrate, then the protease and eventually the inhibitor are present in the solution. Inserting the pins starts the reaction, and removal of the pins from the reaction vessel stops the enzymatic reaction. U.S. Pat. No. 4,546,076 discloses the use of an enzyme assay to monitor the concentration of β-lactam antibiotics present in a sample. U.S. Pat. No. 4,918,001 describes an assay to measure the concentration of endogenous protease inhibitors.

Methods have been described in which the residual protease activity present in a patient sample is measured [see e.g. EP148193; Ther. Drug Monit. 2001, 23(2), 93]. The residual enzyme activity is a measure of the drug effect and patient compliance. This type of assay provides information whether the pathway is sufficiently inhibited. No information regarding the level of said drug in the sample is obtained. This type of assay can only be used for routine monitoring if the target enzyme is readily accessible in a non-invasive manner and is present in said sample in sufficient quantities to enable an enzymatic reaction. Therefore, this approach cannot be readily used for screening HIV protease inhibitors present in a patient sample such as serum, since HIV protease is not present in sufficient quantities in serum.

The use of fluorescent substrates to measure the HIV protease activity was described by e.g. Matayoshi et al. [Science 1990, 247, 954], Tyagi et al. [Anal. Biochem. 1992, 200(1), 143], Toth et al. [Int. J. Pept. Protein Res. 1990, 36(6), 544] and Wang et al. [Tetrahedron 1990, 31(45), 6493] and in several patent publications [see e.g. WO99/67417; EP428000, EP518557]. These disclosures describe how to determine the effect of inhibitors on the HIV protease. These assays are useful for high throughput screening. Whereas in high throughput strategies a positive negative screening, i.e. inhibition or not, is performed, clinical assays need to provide a measure of therapy effectiveness in order to enable the physician to draw conclusions related to the therapy. In screening assays, the concentration of the compound under investigation is known, however, the compound concentration is unknown in clinical samples.

In view of the individualization of patient therapy, there is a need for a flexible approach to determine the amount or concentration of an active ingredient in a biological sample. In addition, there is a need for an assay that also can account for the effect of metabolites of drugs on the bio-active molecule. Therefore, the present invention was made, comprising adding the bio-active molecule to a biological sample, and measuring the activity of the bio-active molecule. In view of the importance to determine the concentration of free and protein bound drugs, the present invention introduces a separation procedure to meet this need.

The instant invention relates to an improved bio-analytical method to determine drug concentrations present in a patient sample. More specifically, the method concerns a fluorescent assay to quantify the inhibitory potency of a biological sample. The method may be used in an integrated approach towards therapeutic drug modeling, linking results of bio-analytical techniques with resistance tests and pharmacological data.

The invention relates to a method for determining the inhibitory potency of an active ingredient in a biological sample, comprising: i) providing a biological sample; ii) providing a bio-active molecule; iii) providing a reagent for the bio-active molecule; iv) adding the biological sample, the bio-active molecule and the reagent for a bio-active molecule to a container; v) determining a signal; vi) relating the signal of v) to a reference standard curve prepared with at least one reference.

According to the present invention a "biological sample" includes any sample derived from an organism i.e. a human or animal, optionally comprising an active ingredient. A biological sample includes but is not limited to blood, serum, plasma, saliva, cerebrospinal fluid, ejaculate, mammary ductal lavage and hair. A biological sample further includes samples obtained from culture flasks, wells, and other types of containers. Said biological sample may comprise one or more active ingredients.

A "bio-active molecule" used in the present invention includes wild type bio-active molecules or recombinant versions thereof. The recombinant versions may include mutations indicative of resistance to one or more active ingredients, may include fluorescent or fluorescence quenching moiety(ies) or may be a fusion construct. The bio-active molecule can be used in conjunction with labeled substrates or ligands in order to provide a homogeneous assay (e.g. fluorescence resonance transfer, FRET; bioluminescence resonance transfer, BRET). A bio-active molecule of the present invention means any biological molecule exhibiting for example enzyme activity e.g. HIV protease, HIV reverse transcriptase, HCV protease (HCV, hepatitis C virus), HCV polymerase, matrix metallo proteinases, renin, thrombin; binding activity or other type of interaction. A bio-active molecule may be provided in a solution e.g. a buffered solution.

A "reagent" for a bio-active molecule includes substrates for enzymes; ligands for receptors. A reagent further includes, co-factors, antibodies, aptamers etc. In one embodiment the reagent is a substrate for HIV protease or a substrate for HCV protease. In one aspect of the invention, the conversion of said substrate by the bio-active molecule may be monitored using fluorescence. The reagent may be provided in a solution. Examples of solutions include buffers, organic solvents, buffered solutions completed with organic solvents.

An "active ingredient" means any compound, including a chemical, drug, antibody, ligand, antisense compound, aptamer, ribozyme, peptide, non-natural peptide, protein, PNA (peptide nucleic acid) and nucleic acids or a composition including at least one compound. This further comprises the compounds as administered and their metabolites. Metabolites may be generated under physiological conditions. As used in the present invention the level of an active ingredient means the amount or concentration of said active ingredient in said sample. The active ingredient present in the biological sample may differ from the active ingredient in the reference. Under these circumstances, the inhibitory potency of the biological sample equals an amount or concentration of active ingredient derived from a reference standard curve. The amount can be expressed as for example, g, ml, mol. The concentration can be expressed for example as ml/ml, g/l, M and the like.

A "matrix" according to the instant invention includes a solution, a buffer, a biological sample including but not limited to blood, plasma, serum, saliva, cerebrospinal fluid, ejaculate, mammary ductal lavage or tissue homogenates or a biological sample further completed with a buffer.

A "container" as used in the invention includes but is not limited to a vessel, a well, a cuvette, a recipient etc. The compounds or liquids may be mixed in said container. Suitably, the determination is performed in said container. The container can be a separate entity e.g. a quartz cuvette or can be arranged in a multiple format such as e.g. a 16 well plate, a 96 well plate, a 384 well plate.

A "signal" means any output generated by the biological assay including fluorescence, fluorescence polarization, time resolved fluorescence, luminescence, time resolved luminescence, absorbance, radioactivity, resonance energy transfer mechanisms, magnetism. In one aspect, the output is generated during the assay. Examples of signals include, absorbance, relative fluorescence units and the like. The signal may be generated by reacting the bio-active molecule with the reagent for the bio-active molecule. A signal may be determined at the end of a predefined incubation period, e.g. after 10 minutes. A signal may be monitored continuously. This includes that a regular time intervals a signal is recorded. This regular time interval includes for instance at predefined time intervals e.g. every 10 seconds, every 5 seconds and the like. A signal may be converted to a ratio of signals. Examples of such ratios include the ratio of a signal generated by a biological sample over the signal generated in a control reaction. A signal may be converted to kinetic variables including initial velocity, maximal velocity, mean velocity.

A "reference" means an active ingredient used to prepare the reference standard curve. The reference is a single compound or a mixture of at least two compounds. Said reference may be present in an identical matrix as the biological sample. Said reference does not necessarily need to be the same active ingredient as present in the biological sample. In one approach the compound used as a reference is the same as the active ingredient present in the biological sample.

A "biological assay" means an assay relying on determining the biological effects generated by a bio-active molecule including the determination of an enzyme reaction, a receptor ligand interaction, DNA polymerase activity, reverse transcriptase activity, integrase activity, antigen-antibody interactions and the like.

"Relating" means that the signal determined, is compared to a reference standard curve, from which curve, the signal can be converted to a measure of inhibition or to a level of reference compound.

"Reference standard curve" includes but is not limited to a curve wherein the signal is plotted against the measure of inhibition. Said measure of inhibition may be expressed as a percentage. The reference standard curve further includes curves in which the signal is plotted against a concentration of reference or an amount of reference. A reference standard curve may also be constructed by plotting a ratio, e.g. a ratio of the signal determined with the biological sample over the signal determined with the control, against a level of an active ingredient. Suitably, said reference standard curve has been prepared according to the procedure of the present invention in particular as recited steps i) to v). Upon preparing a reference standard curve, a reference instead of a biological sample is used in step i). The bio-active molecule and reagent for a bio-active molecule, however, are identical to those used for the analysis of the biological sample. "Corresponding value" includes signal, activity, percentage of inhibition, level of active ingredient present in the reference based on the determination of the reference in the reference standard curve. Said level may be expressed as a concentration (e.g. Molar, g/l, g/g etc.) or as an amount (mol, g, ml, mg, . . . ).

The "inhibitory potency" may be expressed as a percentage of inhibition, as a level of active ingredient i.e. amount or concentration of active ingredient. It is an object of the instant invention that the active ingredient present in the biological sample may differ from the active ingredient used for establishing a reference standard curve. If the active ingredient used for preparing the reference standard curve differs from the active ingredient in the biological sample, the inhibitory potency of the biological sample may be related to an equivalent amount of active ingredient used for preparing the reference standard curve. In such case, the inhibitory potency may be expressed as a drug level, i.e. the signal generated by a biological sample will be related to a corresponding drug level. In one embodiment, the active ingredient used for preparing the reference standard curve is the same as the active ingredient present in the biological sample. In this latter case, the inhibitory potency is equivalent to the level of the active ingredient in the biological sample.

Upon determining the inhibitory potency of an active ingredient in a biological sample, the steps i) to iii) may be put in any order. In step iv), the respective components may be added in different orders. For instance, if a protease activity is determined according to the methods of the instant invention, three components are needed, a biological sample, a protease, and a substrate for the protease. These three components may be brought together in any order, provided that for the purpose of the present invention, the reaction is started with either the bio-active molecule or the reagent for the bio-active molecule. For instance, the biological sample may be first added to the reagent of the bio-active molecule. In this procedure the reaction is started by adding the bio-active molecule to the mixture, and subsequent determination of the signal. It is clear that also the biological sample may be first added to the bio-active molecule. In this approach, the reaction is started by addition of the reagent for the bio-active molecule. It will be clear to the person skilled in the art that in the above procedure instead of adding the biological sample to any of the bio-active molecule or reagent of the bio-active molecule, the reverse may also be performed. For instance, the bio-active molecule may be added to the biological sample, after which the reaction mixture is completed with a reagent of the bio-active molecule.

A blank signal may be determined. This means a reaction without bio-active molecule, e.g. the enzyme, or without reagent for the bio-active molecule. For these purposes, the bio-active molecule or the reagent for the bio-active molecule may be substituted by buffer. Said blank signal may be subtracted from the signal determined when preparing the reference standard curve, or when determining the inhibitory potency of an active ingredient in a biological sample. Said blank signal accounts for the signal generated by the reagent without interaction with the bio-active molecule or reagent for the bio-active molecule.

A control signal may be determined. Said control signal is obtained when no active ingredient is present in the biological sample or in the matrix to prepare the reference standard curve. Said control signal may be used as a 100% value. Alternatively said control signal may be used to obtain ratios of the signals generated with biological samples or with the references to prepare the reference standard curve.

According to one approach, the biological sample is treated with a solvent, such as an organic solvent including methanol, ethanol, to obtain an extract comprising active ingredients. The extract, i.e. the solution comprising active ingredients, is subsequently transferred to a container. Subsequently, in the case of HIV, the inhibitory potency may be determined by measuring the activity of the HIV protease after completing the container with the protease and a substrate for the protease. Both, the extract and the biological sample may need dilution prior to the assay. In one aspect, the biological sample or extract may be diluted to obtain a signal which ranges from about 30% to about 70% of the signal of the control, interestingly from about 40% to about 60% of the signal of the control.

The protease can be a wild-type form or contain one or more mutations. Those mutations may influence the protease activity. In one embodiment a mutant HIV protease may be used. For instance the HIV protease may comprise one or more mutations selected from the list consisting of mutations at amino acid position 3, 10, 20, 24, 32, 33, 35, 36, 37, 46, 47, 50, 53, 54, 57, 58, 63, 70, 71, 72, 73, 77, 82, 84, 88, 89 or 90 vis-à-vis wild type HIV protease (Genbank accession K 03455). The protease can be present in a buffered solution. A buffered solution is used to maintain the pH of the solution constant during the reaction and may be further completed with ions to adjust the ionic strength of the buffer and may be further completed with e.g. anti-oxidants, metal chelators, detergents, co-factors or solvents. Examples of buffers include citrate buffer, phosphate buffer, acetate buffer. The protease may be present in a concentration ranging from about 1 picomolar to about 10 micromolar, suitably ranging from about 1 nanomolar to about 1 micromolar, during the biological assay.

The substrate can also be provided in a solution, a buffered solution, an organic solvent or mixtures thereof. In one approach, the same buffer may be used to prepare the protease solution and the substrate solution. The enzyme activity may be measured using for instance a fluorogenic, quenched fluorogenic or chromogenic substrate. Other methods to measure interactions between a bio-active molecule, its reagent and active ingredient are known in the art and may rely e.g. on FRET, BRET. In these latter approaches, one or both of the interacting compounds may be labeled by a fluorescent molecule. The interaction results in a resonance transfer of the excited wave length. Substrates which are of interest in view of the present invention include those compounds including a moiety selected from the group consisting of 7-amino-4-methylcoumarin, 7-amino-4-carbamoylcoumarin, paranitroanilide, beta-naphtylamide, aminobenzoyl, tetramethylrhodamine, EDANS, DANSYL, fluorescein or DABCYL. The substrate may contain a peptide backbone derived from HIV proteins including gag, protease, reverse transcriptase, integrase, p17, p24 or combinations thereof. Interestingly, said peptide backbone contains 2 to 30 amino acids, suitably 3 to 15 amino acids, more suitably, 3 to 10 amino acids. Examples of such backbones include the sequences S-Q-N-T-P-I-V-N (SEQ ID NO: 1), S-Q-N-Y-P-I-V-W-L (SEQ ID NO: 2) or S-Q-N-Y-P-I-V-Q-K (SEQ ID NO: 3), wherein the amino acids are represented by their one letter code (Practical Biochemistry, $5^{th}$ edition, Ed Wilson & Walker, Cambridge University Press, Cambridge, 2000, p 313). An interesting backbone comprises the amino acid sequence P-I-V (SEQ ID NO: 4). Another interesting backbone comprises the tetrad Y-P-I-V (SEQ ID NO: 5). An interesting substrate is A-R-V-Y-F (NO$_2$)-E-A-Nle (SEQ ID NO: 6) (Nle, norleucine). Self-quenching substrates may also be used (WO 99/50579). Interesting substrates to measure HIV protease include those comprising combinations of DABCYL and EDANS in a peptide backbone; or the combination of aminobenzoyl and nitrophenyl moieties in a peptide backbone. In case HCV protease is determined, substrates may be designed based on the sequence of HCV proteins. Interesting substrates include: (7-methoxycoumarin-4-yl)acetyl (Mca)-D-D-I-V-P-C-S-M-S-(2,4-dinitrophenyl, Dnp) K (SEQ ID NO: 7) and Mca-D-D-I-V-P-C-S-M-K(Dnp)-R-R (SEQ ID NO: 8) (J. Virol. Meth. 1999, 80, 77-84), Ac-D-T-E-D-V-V-P(Nva)-O-4-phenylazophenyl ester (SEQ ID NO: 9) (Ac, acetyl) (Nva, norvaline) (Anal. Biochem. 1999, 270, 268-275), internally quenched depsipeptide fluorogenic substrates based on resonance energy transfer between the donor/acceptor couple 5-[2'-aminoethyl)amino]naphthalene sulfonic acid/4-[[4'-(dimethylamino) phenyl]azo]benzoic acid. Interesting substrates for hepatitis C virus protease are based on resonance energy transfer of depsipeptide substrates (Anal. Biochem. 1996, 240, 60-67). During the biological assay, the substrate may be present in a concentration ranging from about 1 nanomolar to about 500 millimolar, interestingly ranging from about 1 micromolar to about 100 millimolar, more interestingly, from about 10 micromolar to about 1 millimolar.

The method for determining can be performed at room temperature obviating the need for temperature controlled incubating infrastructure. Room temperature includes temperatures in the range from about 17° C. to about 30° C. In one approach, this ranges from about 20° C. to about 26° C. In one approach, the reaction is run at about 25° C. However, the assays can also be performed at other temperatures e.g.

in the range of about 30° C. to about 45° C., in one embodiment between about 35 to about 40° C. or at about 37° C.

The period for incubating may be up to 1 day. In one approach the incubation period is short and ranges from about 15 seconds to about 2 hours, interestingly said period ranges from about 30 seconds to about 60 minutes. During said incubation period the signal may be monitored. Said signal may be monitored continuously, at predefined time intervals or at a single time interval.

The volume during the incubation may be up to 10 ml. An interesting volume ranges from about 10 µl to 5 ml, suitably from about 20 µl to about 2 ml, more suitably from about 25 µl to about 500 µl. In a microtiter plate an interesting volume ranges from about 25 µl to about 300 µl.

The signal of the biological sample may be compared with data on a reference standard curve. Said reference standard curve may be obtained by measuring the signals of a variety of reference samples each comprising a defined drug concentration. Said reference may be present in a matrix such as a solution, a buffer, an organic solvent and the like. In one aspect the reference is present in the same matrix as the biological sample. Said reference standard curve may be prepared using different references, each containing the same active ingredient but at a different concentration. Said reference standard curve may be prepared using at least one reference, suitably, at least two references, each having a different concentration of active ingredient; more suitably at least three references, each having a different concentration of active ingredient. In one aspect the reference standard curve is prepared using 4 to 8 different references of the same active ingredient, each having a different concentration. The active ingredient used for obtaining a reference standard curve can be the same as the active ingredient present in the biological sample. By using a reference standard curve, the method of the current invention makes it possible to relate the generated signal to a specific concentration or amount of active ingredient present in the sample. This reference standard curve can be prepared using any compound or mixture of compounds. Consequently, the inhibitory potency of an active ingredient in a biological sample is a measure of the total inhibitory capacity of a biological sample irrespective the active ingredients present and irrespective their mode of interaction. For enzyme inhibitors said mode of interaction includes irreversible inhibition or reversible inhibition including competitive, non-competitive, anti-competitive, tight-binding or mixed inhibition. Based on such a reference standard curve, an estimate of the level of active ingredient(s) present in a biological sample, irrespective of the knowledge of the nature of the active ingredients, can be determined. This approach can be helpful for e.g. toxicology by indicating that a given biochemical pathway is blocked with an equivalent of a known active ingredient.

Examples of compounds which may be analyzed according to the methods of the instant invention include dextran sulfate, suramine, polyanions, soluble CD4, PRO-542, BMS-806, T20, T1249, 5-helix, D-peptide ADS-J1, AMD 3100, AMD-3465, AMD7049, AMD3451, TAK 779, SHC-C(SCH351125), SHC-D, PRO-140, RPR103611, foscarnet and prodrugs, AZT, 3TC, DDC, DDI, D4T, Abacavir, FTC, DAPD, dOTC, DPC 817, PMEA, PMPA (tenofovir), nevirapine, delavirdine, efavirenz, 8 and 9-Cl TIBO (tivirapine), loviride, TMC-125, dapivirine, MKC-442, UC 781, UC 782, Capravirine, DPC 961, DPC963, DPC082, DPC083, calanolide A, SJ-1366, TSAO, 4"-deaminated TSAO, MV150, MV026048, SP1093V, PD126338, RO-5-3335, K12, K37, L 708906, L 731988, S-1360, anprenavir and prodrug GW433908 (VX-175, fosamprenavir), ritonavir, nelfinavir, saquinavir, indinavir, lopinavir,palinavir, BMS 186316, atazanavir, DPC 681, DPC 684, tipranavir, AG1776, mozenavir, GS3333, KNI-413, KNI-272, L754394, L756425, LG-71350, PD161374, PD173606, PD177298, PD178390, PD178392, PNU 140135, TMC-114, maslinic acid, U-140690, castanospernine, deoxynojirimycine, CGP64222. These compounds may also be included in a kit. Suitably, if HIV protease is used, the active ingredient may be selected from the list comprising: amprenavir, fosamprenavir, ritonavir, nelfinavir, saquinavir, indinavir, lopinavir, palinavir, BMS 186316, atazanavir, DPC 681, DPC 684, tipranavir, AG1776, mozenavir, GS3333, KNI-413, KNI-272, L754394, L756425, LG-71350, PD161374, PD173606, PD177298, PD178390, PD178392, PNU 140135, TMC-114.

Using this assay, monitoring of the reaction kinetics may be performed in real time. Using this approach the steady state variables, e.g. initial velocity may be calculated (Practical Biochemistry, $5^{th}$ edition, Ed Wilson & Walker, Cambridge University Press, Cambridge, 2000, Chapter. 7, p. 357-402). In one embodiment, the reaction is stopped before determining the signal. This is an end-point determination. A reaction may be stopped by adding an agent including an organic solvent, detergent, acid, base or by temperature changes. The output e.g. fluorescence can be recalculated to parameters describing the reaction e.g. initial velocity, or to measures of inhibition e.g. percentage inhibition or percentage residual activity.

The assay may also be used to determine concurrently 2 or more active ingredients, present in a biological sample, targeted against 2 or more bio-active molecules. For this purpose, 2 or more different substrates may be used, each of which can be measured independently. Based on 2 or more reference standard curves, the two or more active ingredients may be quantified. For example, the inhibitory potency of biological sample comprising both an HCV protease inhibitor and an HIV protease inhibitor may determined in a single well, using two different substrates. One substrate is specific for HIV protease and one substrate is specific for HCV protease.

A further advantage of the present method is that it allows determining the amount of active ingredients bound to plasma proteins. Many compounds are heavily protein bound, limiting their therapeutic efficacy. HIV protease inhibitors may be protein bound. An example of an HIV protease inhibitor binding protein is α-acid glycoprotein (AAG). The sample may be treated to separate the free from the protein bound active ingredients. This separation can be performed by filtration. Filtration may be performed using gels e.g. gel filtration, filters, filter papers, using special microtiter plates. Other techniques are available in the art such as dialysis, heating, precipitation, centrifugation, antibodies and other means known to the person skilled in the art. Also combinations of said techniques may be used to separate the protein bound from the unbound active ingredient. The differentiation of the free over the protein bound fraction may be important for compounds which are subject to protein binding and in conditions wherein the protein concentration or the concentration of a particular protein varies over time in a bodily fluid. The knowledge of the distribution of the compounds between free and bound may be important in evaluating a therapy, especially if only the active ingredient is accessible to its target.

Since the bio-active molecule is added to the reaction mixture, the bio-active molecule does not necessarily need to be present in the sample. The method of the present invention further provides an assay for those instances where the bio-active molecule is not readily accessible or is present in too low a concentration in a biological fluid like e.g. serum which may contain HIV inhibitors but only a very low amount if any of the protease. Alternatively, the method may be used following removal from the biological sample of the bio-active molecule concerned or following inactivation of the bio-active molecule. These latter approaches may be valuable in those instances where the concentration of said bio-active molecule varies between individuals. Removal or inactivation may be achieved by different methods including but not limited to precipitation by organic solvents, salts, detergents, change of pH or thermal denaturation.

In one approach, the assay of the instant invention is homogenous, has a short turnover time and facilitates the parallel processing of multiple samples. The assay of the instant invention can be run in a cuvette based format or in multi-well format e.g. a microtiter plate.

The assay design is such that it determines the presence i.e. the level of active ingredients inhibiting the enzyme in biological samples and is especially suited for monitoring active ingredients in individuals under treatment as well as in individuals subject to clinical trials. The determination of the concentration can provide evidence whether the dosage of the compound is high enough to provide a therapeutic effect.

The instant invention also relates to a kit comprising a bio-active molecule, a reagent for said bio-active molecule, and optionally an active ingredient. The bio-active molecule, the reagent, and the active ingredient may be present in separate containers. The bio-active molecule, the reagent, and the active ingredient may be lyophilized. The kit may be further completed with a container comprising a buffer for the enzymatic reaction. Said buffer may be provided as a lyophilized powder. If the kit is composed of lyophilized components, said kit may be further completed with one or more solutions for the dissolution of said lypohylized powders. The kit may contain one or more containers comprising one or more active ingredients. The container comprising the active ingredient, needed to prepare a reference standard curve, may optionally contain the protease or the substrate for the protease.

Another level of complexity in diseases like cancer and HIV, is the frequent occurrence of resistance towards treatment. These latter conditions require a frequent monitoring of drug levels in conjunction with resistance testing. Therefore, methods have been developed which monitor the phenotypic alterations in the population of HIV virions circulating in the patient (e.g. WO 97/27480). Other phenotyping assays include those described by Witvrouw (WO 01/57245), Virologic (WO97/27319) and Bioalliance (WO 02/38792). The Antivirogram® (WO97/27480) estimates the drug susceptibility of the viral population, as compared to 'wild-type' strains. In this test service, the drug concentration that inhibits virus growth for 50% ($IC_{50}$) is determined in vitro. The ratio $IC_{50}$ of the virus in a patient's blood sample over the $IC_{50}$ of 'wild-type' virus is the fold change in drug susceptibility of the virus in that patient. An alternative for the phenotypic assays in which the patient borne material is grown under in vitro conditions, is genotyping. Genotyping assays estimate the occurrence of resistance based on sequence variations. One improvement over the genotypic assays is called VirtualPhenotyping (WO 01/79540) in which the genotype of a patient virus is compared to a collection of genotypes present in a database and for which the corresponding phenotypes are stored in a database. These assays provide an accurate determination of the drug effect and the occurrence of resistance of the virus in a patient, yet no information on circulating drug levels are provided. Therefore, it is an aspect of the instant invention to link drug level determinations, according to the methods of the present invention, to resistance testing. Linking the determination of drug levels to resistance testing can provide additional evidence of the therapy efficacy.

The minimum plasma concentration or trough concentration can be critical during treatment of diseases or conditions wherein the drug target is subject to modulation in order to overcome the drug effect. Examples of this latter phenomenon are found in infectious diseases like HIV, bacterial infections and cancer. For example, the presence of drugs generates mutational pressure on the HIV protease to escape from drug therapy and insufficient inhibitor concentration facilitates such escape. The determination of the drug level in a patient and the use of this value to determine the trough level can be important in obtaining dosages high enough to yield a therapeutic effective concentration.

The concentration of an active ingredient, determined using the procedure of the instant invention, can be used in pharmacological models to provide estimates of pharmacokinetic parameters describing the drug profile in an individual. Using population pharmacokinetic models, the trough drug level can be determined from a single patient sample. Suppose a large group of HIV-infected patients receive the same antiretroviral drug in the same dose three times daily. The average plasma concentration-time profile of the drug in the patient population may look as shown in FIG. 1 (bold line). However, due to the inter-individual variability of pharmacokinetic processes (absorption, distribution, elimination), individual curves may substantially differ from the typical profile, as exemplified by the dotted line. If all individual curves are plotted, they may cover a range marked by the vertical bars. If on the same graph, individual minimum effective concentrations (MECs) (dashed horizontal line gives an example, FIG. 1) are provided, they will also cover some range. The drug concentration in a fraction of the patients may drop below their MEC and this reduces the therapeutic outcome, and possibly leads to drug resistance. The trough level of an individual patient can subsequently be used to calculate the drug level required to attain therapeutic effective doses during the dosing interval.

The methods and results of the instant invention, e.g. the concentration of a drug, may be used to determine pharmacological parameters of the drug in an individual, including trough levels ($C_t$), maximal concentration ($C_{max}$), the area under the curve (AUC), elimination velocity etc. Therefore, the determined level may be inputted in a population pharmacokinetic model and pharmacokinetic variables such as $C_t$, $C_{max}$, AUC may be calculated (WO 02/23186). These pharmacological variables may be used to estimate for example the potential toxicity of a certain dose, exposure time to a drug (e.g. in case of radiochemicals) or minimum concentration found.

In order to obtain effective treatment, the exposure of an individual to a drug e.g. trough concentration, AUC, must exceed a certain level. This level is determined by the nature of the virus population. The ratio of the exposure to the drug (trough level, AUC, other) over the drug-resistance (fold-resistance, $IC_{50}$, $IC_{90}$, other) is predictive for successfulness of the therapy. This ratio can be expressed as the IQ (inhibitory quotient) ($IQ=C_t/IC_{50}$.). This IQ value can be further normalized in order to obtain a value adjusted for protein binding (normalized IQ, NIQ). One approach of obtaining this adjusted value is to determine the mean $C_t$ for a population, and the $IC_{50}$ for an active ingredient for a reference strain i.e. a reference laboratory HIV strain. The quotient of these latter two values yields $(C_t/IC_{50})_{reference}$.

The normalized IQ is provided by the quotient: $[(C_t/IC_{50})]_{patient}/[(C_t/IC_{50})]_{reference}$.

In one embodiment, the instant invention provides a method for determining the inhibitory quotient (IQ), wherein the trough level is based on the level of the active ingredient present in a biological sample determined according to the methods described herein. The IQ can be further normalized.

The invention further provides a method of designing a therapy, the method comprising: determining the level of an active ingredient present in a biological sample according to the methods described herein, determining the trough level for said active ingredient, recalculating the dosage for said active ingredient using a population kinetic model to achieve active ingredient levels exceeding the minimal effective dose during the dose interval.

In a further development the concentration found in the patient sample may be transmitted electronically to a server where the pharmacokinetic values are determined through population based methods. These values i.e. pharmacokinetic data and drug levels may be linked to resistance data to provide an integrated measure of therapy efficacy. The provided information may be further used to design a therapy in order to achieve sufficient clinical effect. These data may, following processing, be transferred back to e.g. the treating physician.

The assay may be used for analysing drug levels in animals and pharmacokinetic studies in animals.

In one aspect, the present invention concerns a method of determining the inhibitory potency of a biological sample, the method comprising: (a) obtaining a biological sample, providing a container comprising a target bio-active molecule, adding the biological sample to said container to obtain a mixture, adding a reagent of the bio-active molecule to the mixture and determining a signal, (b) relating the signal to a reference standard curve prepared with at least one reference sample, wherein the reference sample has the same matrix as the biological sample, the matrix optionally completed with an active ingredient at a defined concentration, and wherein the signal of the reference sample has been determined according to (a).

The assay procedure can be used to monitor interactions between enzyme, substrate and inhibitor but equally well between receptor and ligand; receptor and antagonist; receptor and agonist; antigen and antibody. For the analysis of active ingredients interacting with receptor molecules, ligands instead of substrates are preferred for the analysis method of the present invention.

In one embodiment, the assay of the instant invention adds to the art a flexible, fast, easy to standardize, economical and homogenous assay to monitor drug levels in patient samples using an enzyme. Multiple assays can be run in parallel and inter-laboratory variation can be limited by providing kits containing the required elements to perform the reaction.

FIGURES

FIG. 1: Plasma concentration of active ingredient (mg/l) as a function of time. MEC is the minimum effective concentration. The time is expressed in hours. The plasma drug concentration should vary between the MEC and the toxic level.

Figure 2:
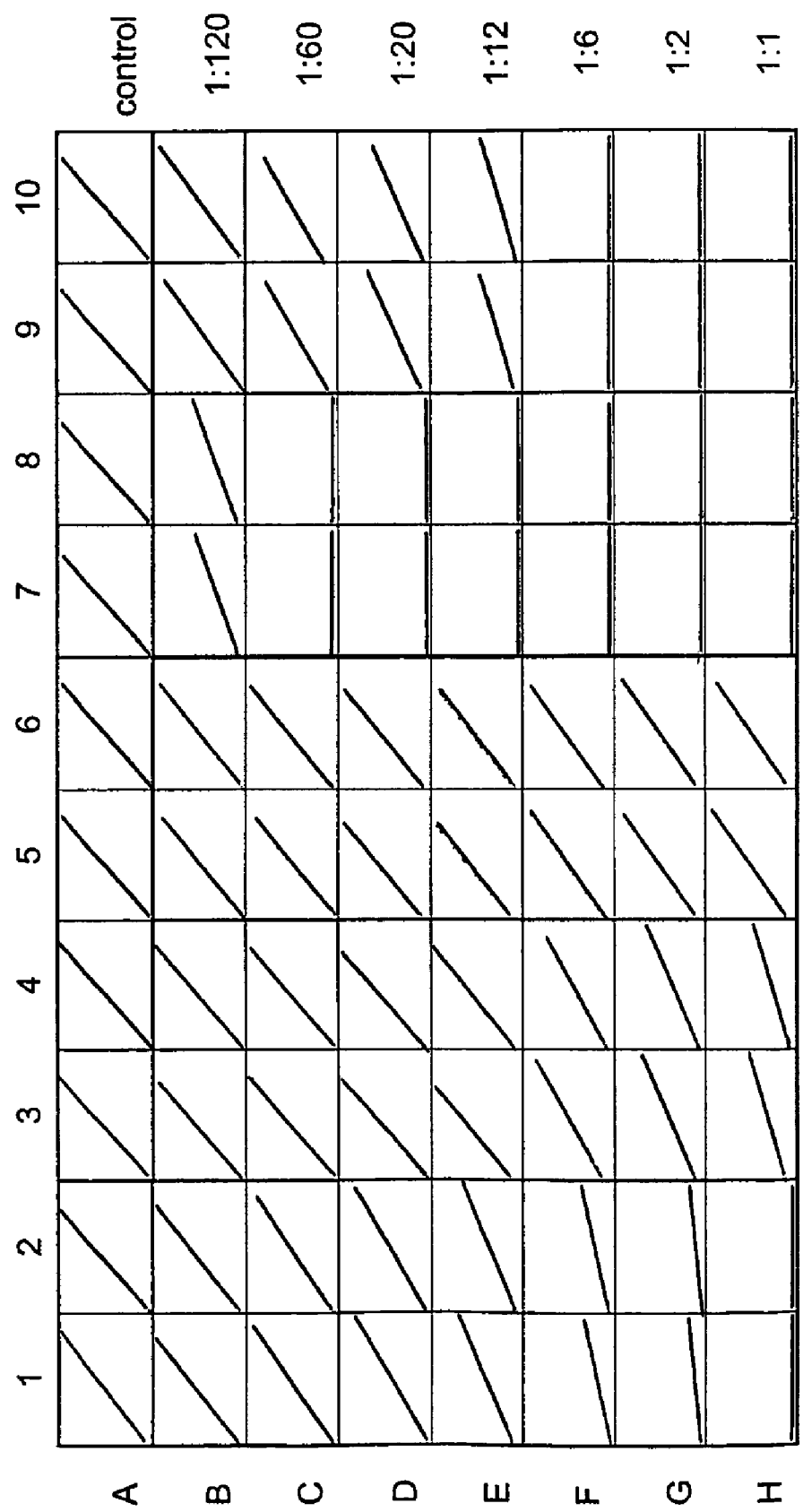

FIG. 2: Monitoring of substrate cleavage by HIV protease in real time in a fluorescence microtiter plate reader. Each square (A1 tot H10) represents the progress curves of the fluorescence (Y-axis) as a function of time (X-axis). The assay was run as described in the experimental part. The slope of each curve represents the initial velocity of the enzymatic reaction. Row A contains control samples Without inhibitor. Columns 1 and 2 contain extracts of dog serum spiked with different concentration of compound 1 used to generate a calibration curve. Columns 3 and 4; 5 and 6; 7 and 8; 9 and 10, contain dog serum spiked with 100 nM, 10 nM, 10,000 nM, and 1,000 nM of compound 1,2 and 3 respectively. Row B to H contain dilutions of the spiked serum as indicated at the right. The dilutions vary from 1:120 (row B) to 1:1 (row H). See example 1 for details.

Figure 3:
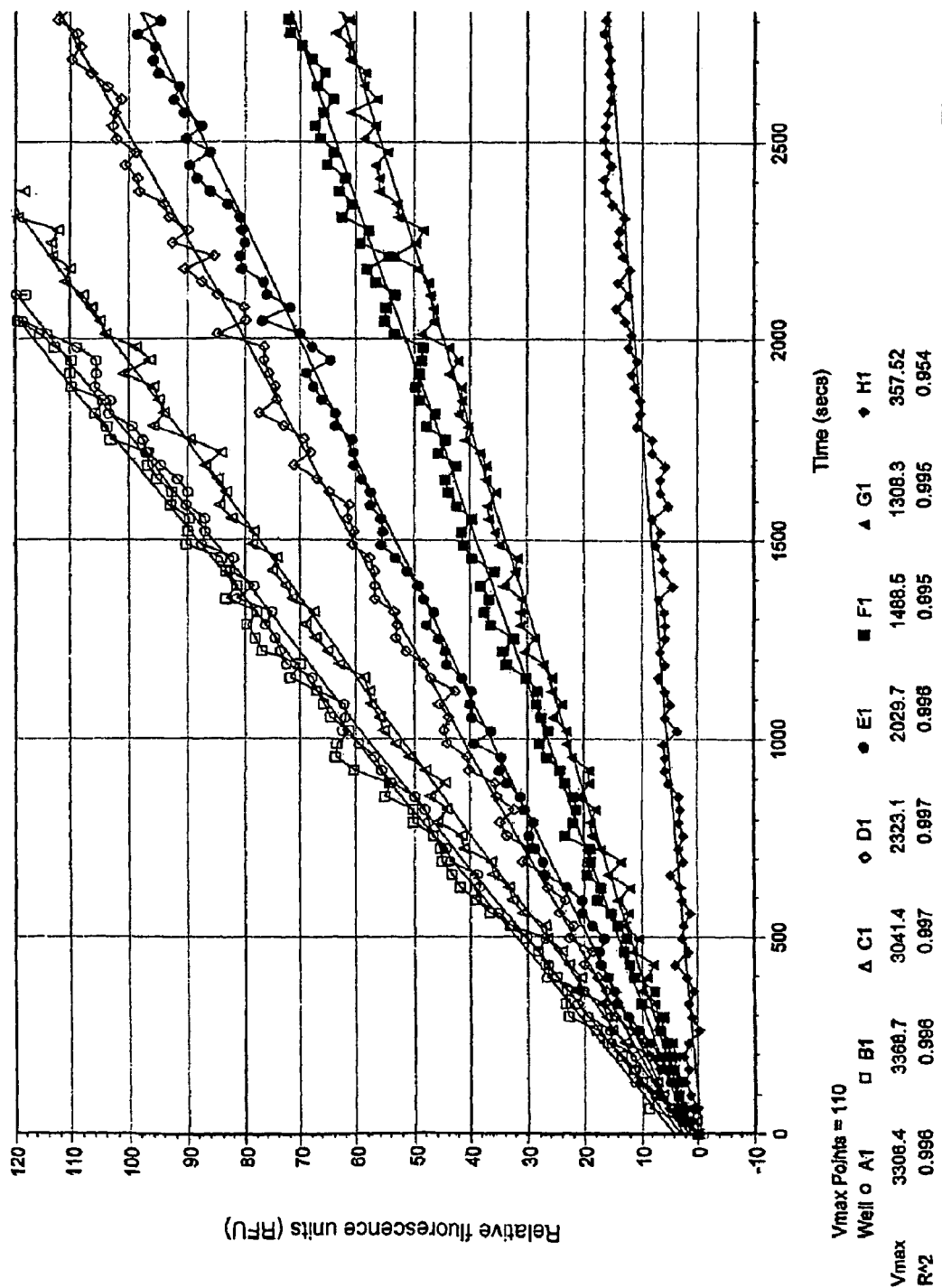

FIG. 3: Initial rate of substrate cleavage calculated using linear regression by plate reader software. The substrate cleavage was monitored in real time in a fluorescence microtiter plate reader. Extracts of dog serum spiked with different concentrations of compound 1 were used. The relative fluorescence units (RFU, Y-axis) were monitored as a function of time (seconds, X-axis).

FIG. 4: Calculation of a reference standard curve, the data further illustrate the accuracy of the captioned method. Sa: sample; concentration in nM; Values: in (RFU/min)×1000; StDev (standard deviation): in (RFU/min)×1000; CV %: coefficient of variation; MeanValue: mean Value in (RFU/min)×1000; Ratio: ratio of the MeanValue of Sa0X over the MeanValue of Sa01. X is 2 to 8 (see figure).

Figure 5:
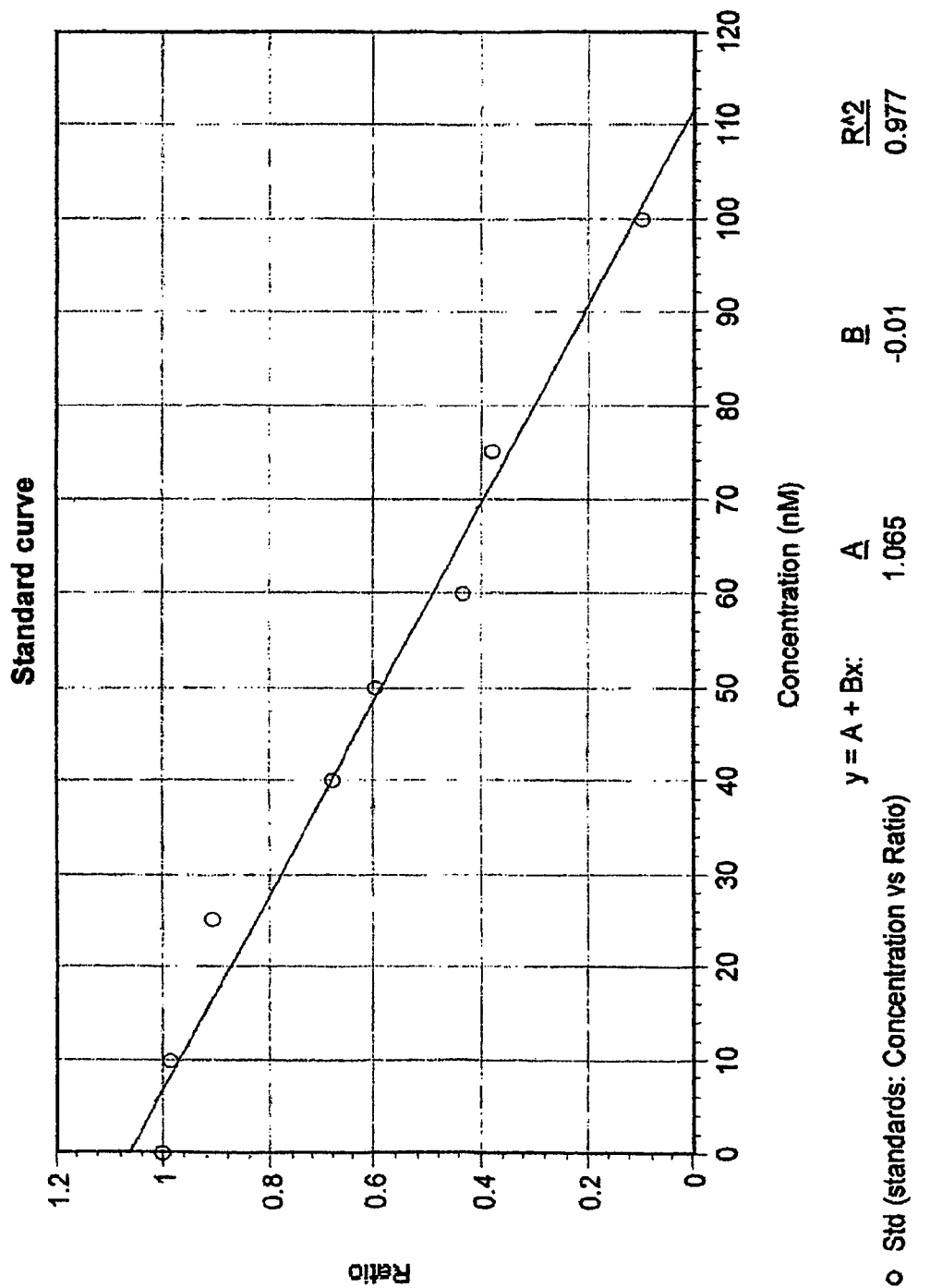

FIG. 5. Typical reference standard curve relating the concentration of inhibitor in nM (X-axis) to the ratio of test sample compared to a control sample (expressed as a ratio of RFU values, Y-axis)

FIG. 6: Calculation of analyte concentration. The calculation of the analyte is performed automatically by the plate-reader software. Concentration was calculated for analyte presented in columns 9 and 10 on FIG. 2. The data show that samples may need to be diluted prior to analysis. In the present case a dilution between 6 to 60 is optimal. (StDev=Standard deviation; Adj. Result=result adjusted for dilution).

FIG. 7: Accuracy and precision of the method. Five independent experiments were performed on five different dates to assess the accuracy and reproducibility of the method.

Exp.: experiment. The error of each determination is shown in parenthesis and represents the difference between measured inhibitor concentration and spiked inhibitor concentration expressed in %.

EXAMPLES

The present example and accompanying drawings illustrate the present invention. Their illustrative purpose is not construed as limiting the scope of the invention.

Example 1

Determination of HIV PR Inhibitor (Human Immunodeficiency Inhibitor, HIV; PR, Protease), Concentration in Serum Samples The following compounds were used in the present analysis (3R,3aS,6aR)-hexahydrofuro[2,3-b]furan-3-yl-N-[(1S,2R)-3-[[(4-aminophenyl)sulfonyl](2-methylpropyl)amino]-2-hydroxy-1-(phenylmethyl)propyl]-carbamate, (compound 1, CAS 206361-99-1); (3R,3aS,6aR)-hexahydrofuro[2,3-b]furan-3-yl-N-[(1S,2R) -3-[(1,3-benzodioxol-5-ylsulfonyl)(2-methylpropyl)amino]-2-hydroxy-1-(phenylmethyl)propyl]-carbamate (compound 2, CAS 333798-27-9) and (3R,3aS,6aR)-hexahydrofuro[2,3-b]furan-3-yl-N-[(1S,2R)-2-hydroxy-3-[[(4-methoxyphenyl)sulfonyl](2-methylpropyl)amino]-1-(phenylmethyl)propyl]-carbamate (compound 3, CAS 206362-00-7). The method of the present invention may also be used with other sulfonamides as described in U.S. Pat. No. 5,843,946. Four aliquots of normal dog serum were spiked with HIV PR inhibitor compound 1, to final concentration of 10, 100, 1,000 and 10,000 nM (referred later as analyte samples) respectively. Another 8 aliquots of dog serum were used to generate a reference standard curve. These 8 aliquots were spiked with different concentration of compound 1 from 0 to 100 nM. Thus compound 1 was used as reference to prepare a reference standard curve. Serum proteins in all samples were precipitated using 66% (v/v) methanol (MeOH). To one part of serum sample two parts of MeOH were added, mixed and centrifuged at 16,100 g for 30 min. The supernatant was recovered and can be stored for at least 2 weeks at −20° C. prior to assay. 60 µl is used for the cuvette assay or 24 µl is used for the plate reader assay. Six serial dilutions 1:2 to 1:120 of the extracts, obtained from analyte samples were prepared prior to assay. Methanol extract of normal dog serum without inhibitor was used for the dilution.

For the plate reader assay, the following conditions were used: The buffer was prepared of 50 mM Sodium acetate (NaOAc), pH 4.5, 2 mM dithiothreitol (DTT), 20 mM Sodium Chloride (NaCl), 0.01% Tween 20. The substrate was present at a final concentration of 20 µM in the above buffer. The substrate used is based on a natural substrate for HIV protease. It contains a portion ($P_4$-$P_4'$) of the p17-p24 gag protein. R-E(EDANS) -S-Q-N-Y-P-I-V-Q-K(DAB-CYL)-R-OH (SEQ ID NO: 10) displays only low fluorescence, yet upon cleavage by HIV protease at Y-P bond fluorescence augments (Science, 1989, 247, 954-958). The enzyme, wild type HIV-1 protease, was present in the above buffer (50 mM NaOAc, pH4.5, 2 mM DTT, 200 mM NaCl), 0.01% Tween 20) at a final concentration of 4-5 nM. It should be appreciated that other forms of HIV protease can be used as well, including mutant forms of the protease.

The assay is performed at room temperature (RT). 88 µl of buffer (which contains the enzyme) were dispensed and 24 µl of serum extract or serum extract dilution was added using multi-channel pipettor. The reaction was started by adding 88 µl buffer containing substrate and the increase of fluorescence was monitored over time (FIG. 2). The reference standard curve was prepared according to this method using 24 µl of reference instead. The control reaction consisted of extracted serum void of any protease inhibitor. Initial rate of substrate cleavage, that was calculated by the plate reader software for each well (FIG. 3) was inverse proportional to inhibitor concentration. The initial rate of control sample provided a 100% signal and was used to determine the ratio with respect to the samples from the reference standard curve as well as from analyte samples, containing an inhibitor (ratio signal sample/signal control).

The initial rate of fluorescence increase was monitored for each compound 1 dilution (FIG. 2, columns 1 and 2) to yield a reference standard curve (FIG. 4, 5). The reference standard curve links the ratio (signal sample/signal control) to the drug concentration for each compound 1 dilution. The measure of inhibition, expressed as a ratio, provides an estimate of the corresponding concentration of compound 1. For example, the concentration of inhibitor in analyte sample presented in columns 9 and 10 on FIG. 2, can be calculated using plate reader software as shown on FIG. 6. For the final calculation two concentrations that gave the ratio closest to 0.5 were averaged. The resulted calculated concentration was 1,109 nM, comparable to actual concentration in this sample—1,000 nM. Note that the reference standard curve can be prepared using any protease inhibitor or mixture thereof.

Though, the above assay does not discriminate between different HIV protease inhibitors, it provides a reliable and accurate determination of HIV protease inhibition and concurrently the level of the inhibitory activity in the biological sample. This assay format determines the total amount of protease inhibitor present in a biological sample. In addition, the assay can provide evidence on the percentage of protein bound inhibitor as exemplified in Example 3.

Determination of inhibitor concentration as described in Example 1 was performed on five different days to evaluate precision and accuracy. The results are presented on FIG. 7.

The principle of the present invention can be used to any type of compound interfering with a bio-active molecule. It will apparent that the person skilled in the art will know different approaches of working the instant invention.

Example 2

Effect of MeOH

The methanol extraction is commonly used for determination of HIV PR inhibitor concentrations in human serum by LC-MS. Serum proteins are precipitated with 75% MeOH. Since high concentration of methanol can interfere with enzyme-based assays, the MeOH concentration used for the extraction of inhibitors was reduced to 66%. Following test was performed to compare the extraction with 66% MeOH and 75% MeOH. Mixtures of compound 1 and 2 were prepared at 9 µM and 0.9 µM concentrations and extracted with 66 and 75% MeOH as described in example 1. The results are summarized in Table 1. "Ext" means extraction in Table 1.

TABLE 1

| Inhibitor | Control (in µM) | % error | 66% Ext (in µM) | % Error | 75% Ext (in µM) | % Error |
|---|---|---|---|---|---|---|
| 9 µM | 8.94 | 0.6 | 10.5 | 16.6 | 8.34 | 7.3 |
| 0.9 µM | 0.85 | 5.5 | 0.99 | 10 | 0.77 | 14.4 |

Example 3

Determination of Protein Bound Versus Total Drug Concentration

According to multiple studies most of HIV PR inhibitors are highly plasma protein bound (e.g. 90-99% for amprenavir, nelfinavir, saquinavir and ritonavir and about 60% for indinavir (IDV)). Since protein binding affects the drug potency, a simple method for the determination of plasma protein bounded versus unbounded drug concentration was developed. Following protocol was used to measure the unbound drug concentration:

550 µl of normal human serum was spiked with the protease inhibitor SC-52151 at final concentration 1 µM. 50 µl aliquot was used for the total inhibitor concentration determination as described in example 1. SC-52151 was used to generate a calibration curve.

500 µl spiked serum sample was loaded on microcon-10 microconcentrator and spun @5000×g, at room temperature for 5 min. The flow through fraction (~10% of load, 50 µl) was extracted with 66% methanol according to the protocol described in example 1. The filtrate contains the unbound fraction of protease inhibitors. Different dilutions of methanol extract were prepared and the micro titer plate reader assay was performed to determine unbound or free drug concentration as described in example 1. As in the case of total inhibitor concentration (example 1), the unbound drug concentration is presented as an inhibitory activity equivalent to reference drug concentration (in this case the inhibitory activity equivalent to a SC-52151 concentration in nM derived from the calibration curve). Using the methods of the instant invention the ratio of the free versus total drug concentration can be determined and expressed as a percentage.

TABLE 2

Percentage of HIV protease inhibitor in sample not bound to proteins

| Sample (spiked with 1 µM drug) | IDV | SC-52151 |
|---|---|---|
| Free/total drug ratio (%) | 36.5 | 10.5 |

The free indinavir concentration (36.5%) is in good agreement with data present in the literature (40%). In human serum, HIV protease inhibitors are primarily bound to α-acid glycoprotein. The free drug concentration determined in these experiments is inversely proportional to the binding constant of the drug to alpha-acid glycoprotein. $K_a$ is the binding constant.

| | IDV | SC-52151 |
|---|---|---|
| $K_a$ for AAG binding ($10^6$ $M^{-1}$) | No binding | 2.3 |

The invention claimed is:

1. A method for determining the inhibitory potency of an HIV inhibitor in a biological sample, comprising:
   i) providing a biological sample comprising said HIV inhibitor;
   ii) providing HIV protease;
   iii) providing a substrate for HIV protease R-E(EDANS)-S-Q-N-Y-P-I-V-Q-K(DABCY-L)-R-OH (SEQ ID NO: 10);
   iv) separating HIV inhibitor bound to proteins in the biological sample from unbound HIV inhibitor by gel filtration, filters, filter papers, special microtiter plates, dialysis, heating, precipitation, centrifugation, or antibodies or by combinations thereof;
   v) adding the resulting biological sample from which bound HIV inhibitor has been separated, the HIV protease and the HIV protease substrate to a container;
   vi) determining a signal; and
   vii) relating the signal of vi) to a reference standard curve prepared with at least one reference.

2. The method according to claim 1, wherein the HIV protease comprises at least one mutation.

3. The method according to claim 1, wherein the signal in fluorescence.

4. The method according to claim 1, wherein the container is a well in a multi-well plate.

5. The method according to claim 1, wherein the biological sample comprises a reversible inhibitor.

6. The method according to claim 1, wherein the reference for determining the reference standard curve has the same biological matrix as the biological sample.

7. The method according to claim 1, wherein the inhibitory potency is expressed as drug concentration or as a drug amount.

8. A method for determining a trough level of a drug in an individual using a population pharmacokinetic model, characterized in that the drug concentration or drug amount is determined according to claim 7.

9. The method for determining the inhibitory quotient of a drug in a biological sample, using the trough level of the drug in an individual determined according to claim 8.

10. A method for designing a therapy, comprising: determining the trough level of a drug in an individual according to claim 8, recalculating the dosage for the drug using a population kinetic model, achieving drug levels exceeding the minimal effective dose during the dose interval.

11. A method for determining the inhibitory potency of an HIV inhibitor in a biological sample, the method comprising:
   (a) obtaining a biological sample comprising HIV inhibitor, separating HIV inhibitor bound to proteins in the biological sample from unbound HIV inhibitor by gel filtration, filters, filter papers, special microtiter plates, dialysis, heating, precipitation, centrifugation, or antibodies or by combinations thereof, providing a container comprising a HIV protease, adding the resulting biological sample from which bound HIV inhibitor has been separated to said container to obtain a mixture, adding the HIV protease substrate R-E-(EDANS)-S-Q-N-Y-P-I-V-Q-K(DABCYL)-R-OH (SEQ ID NO: 10) to the mixture and determining a fluorescence signal, and
   (b) relating the signal to a reference standard curve prepared with at least one reference sample,
   wherein the reference sample has the same matrix as the biological sample, the matrix optionally completed with an active ingredient at a defined concentration, and wherein the signal of the reference sample has been determined according to (a).

12. The method according to claim 11, wherein the signal is fluorescence.

13. The method according to claim 11, wherein the container is a well in a multi-well plate.

14. The method according to claim 11 wherein the biological sample comprises a reversible inhibitor.

15. The method according to claim 11, wherein the reference for determining the reference standard curve has the same biological matrix as the biological sample.

16. The method according to claim 11, wherein the inhibitory potency is expressed as drug concentration or as a drug amount.

* * * * *